(12) United States Patent
Junkins

(10) Patent No.: US 7,114,506 B2
(45) Date of Patent: Oct. 3, 2006

(54) VIBRATORY CLEANING DEVICES AND METHODS

(76) Inventor: Mitch Junkins, The CDM Company, 12 Corporate Plz., Suite 200, Newport Beach, CA (US) 92660

( * ) Notice: Subject to any disclaimer, the term of this patent is extended or adjusted under 35 U.S.C. 154(b) by 0 days.

(21) Appl. No.: 10/783,276

(22) Filed: Feb. 20, 2004

(65) Prior Publication Data

US 2005/0000537 A1    Jan. 6, 2005

Related U.S. Application Data

(60) Provisional application No. 60/540,866, filed on Jan. 30, 2004, provisional application No. 60/523,046, filed on Nov. 17, 2003, provisional application No. 60/485,361, filed on Jul. 2, 2003.

(51) Int. Cl.
   *A61C 15/00* (2006.01)
(52) U.S. Cl. ........................ 132/322; 132/326
(58) Field of Classification Search ................ 433/118, 433/119, 120, 121, 122, 123, 124; 132/322, 132/323–327; 606/161; 15/22.1, 22.2; 601/142
   See application file for complete search history.

(56) References Cited

U.S. PATENT DOCUMENTS

| 3,183,538 | A |   | 5/1965  | Hubner ................... 15/22 |
| 3,466,689 | A |   | 9/1969  | Aurelio et al. ............. 15/22 |
| 4,555,697 | A | * | 11/1985 | Thackrey .................. 340/575 |
| 5,188,133 | A | * | 2/1993  | Romanus ................... 132/325 |
| 5,261,430 | A | * | 11/1993 | Mochel .................... 132/322 |
| 5,267,579 | A | * | 12/1993 | Bushberger ................ 132/322 |
| 5,343,883 | A | * | 9/1994  | Murayama ................. 132/322 |
| RE35,712  | E |   | 1/1998  | Murayama ................. 132/322 |
| 5,947,912 | A | * | 9/1999  | Montagnino ............... 601/142 |
| 5,987,681 | A | * | 11/1999 | Hahn et al. ............... 15/22.1 |
| 6,421,865 | B1| * | 7/2002  | McDougall ................ 15/22.1 |
| 2002/0106607 | A1 |   | 8/2002 | Horowitz ................... 132/322 |
| 2002/0120991 | A1 | * | 9/2002 | Cacka et al. .............. 15/22.1 |
| 2002/0170570 | A1 | * | 11/2002 | Bergman ................... 132/322 |

* cited by examiner

*Primary Examiner*—Cary E. O'Connor
(74) *Attorney, Agent, or Firm*—Rutan & Tucker, LLP

(57) ABSTRACT

A flossing device has an internal supply of floss, a pair of tines between which a length of the floss is strung, and a vibration source that causes the floss to vibrate at a frequency of least 10 Hz. In another aspect, a dental cleaning device has three separable parts—a handle, a neck section, and a plurality of interchangeable cleaning heads. The handle has a power source that is in electronic communication with the neck section, and the neck section houses a vibration source that is received by the interchangeable cleaning heads.

15 Claims, 4 Drawing Sheets

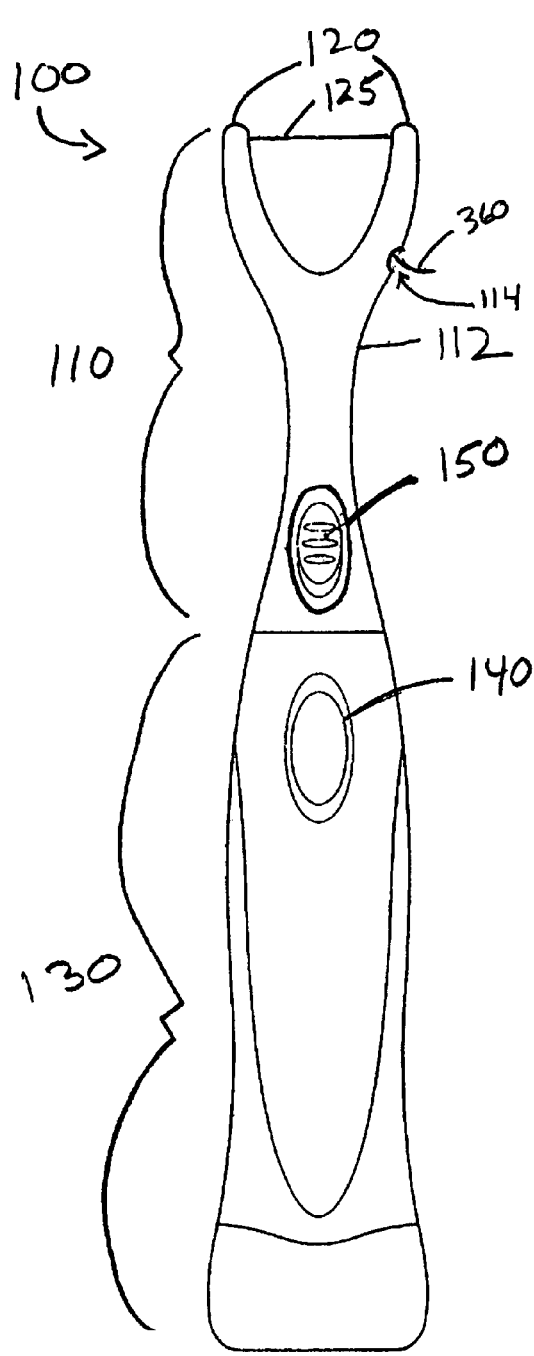
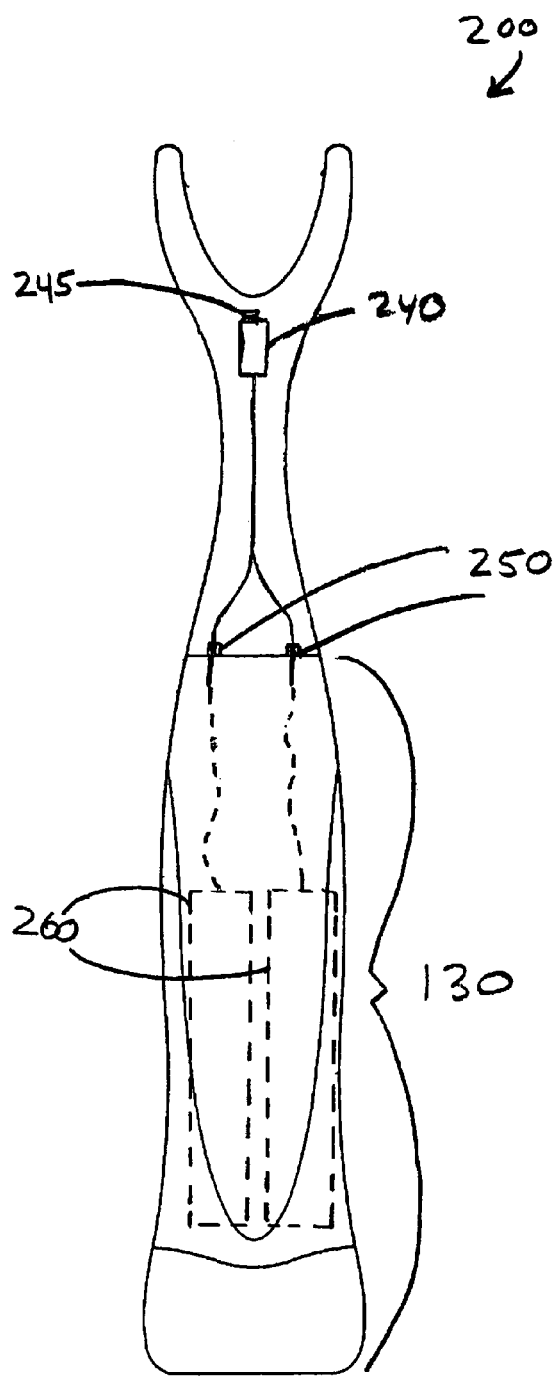
Fig. 1
Fig. 2

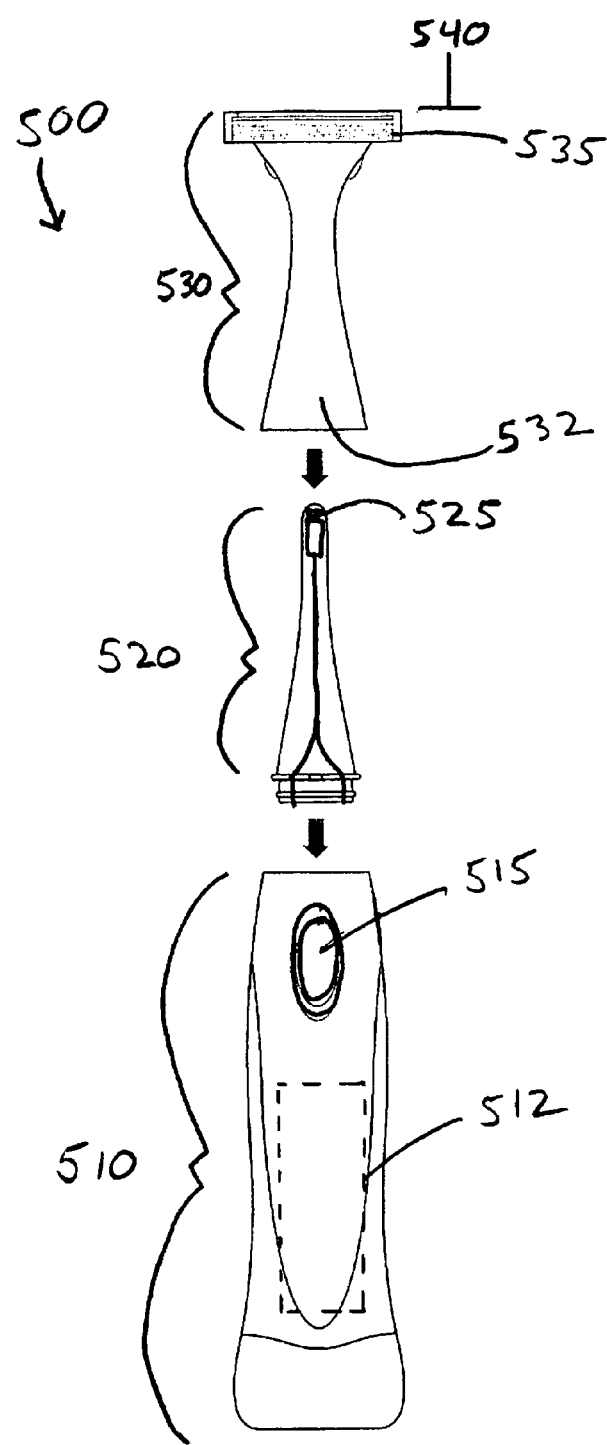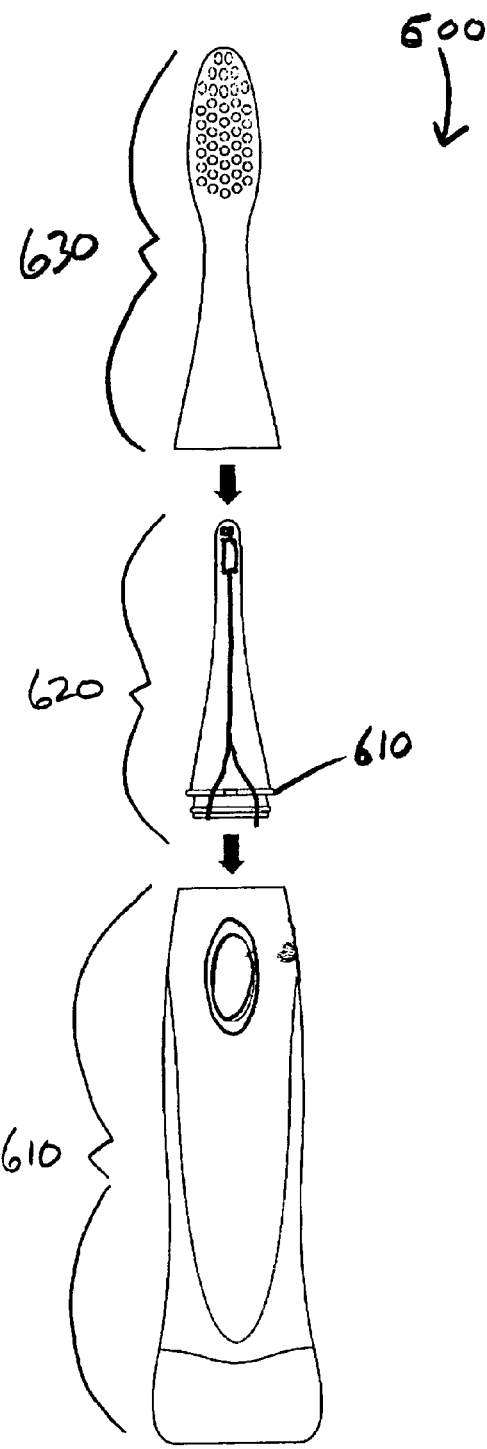
Fig. 5
Fig. 6

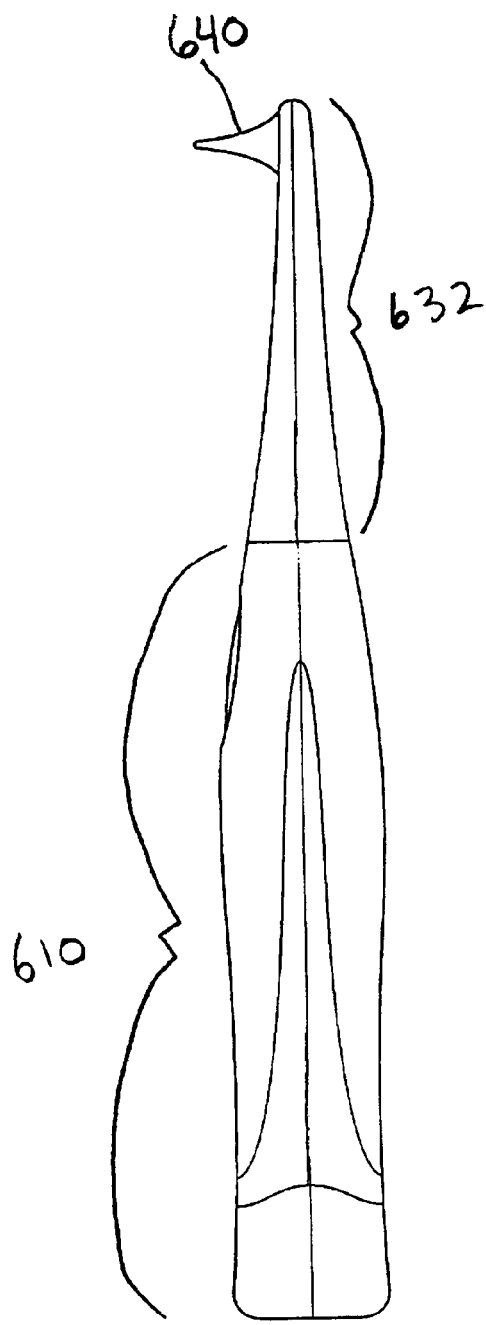
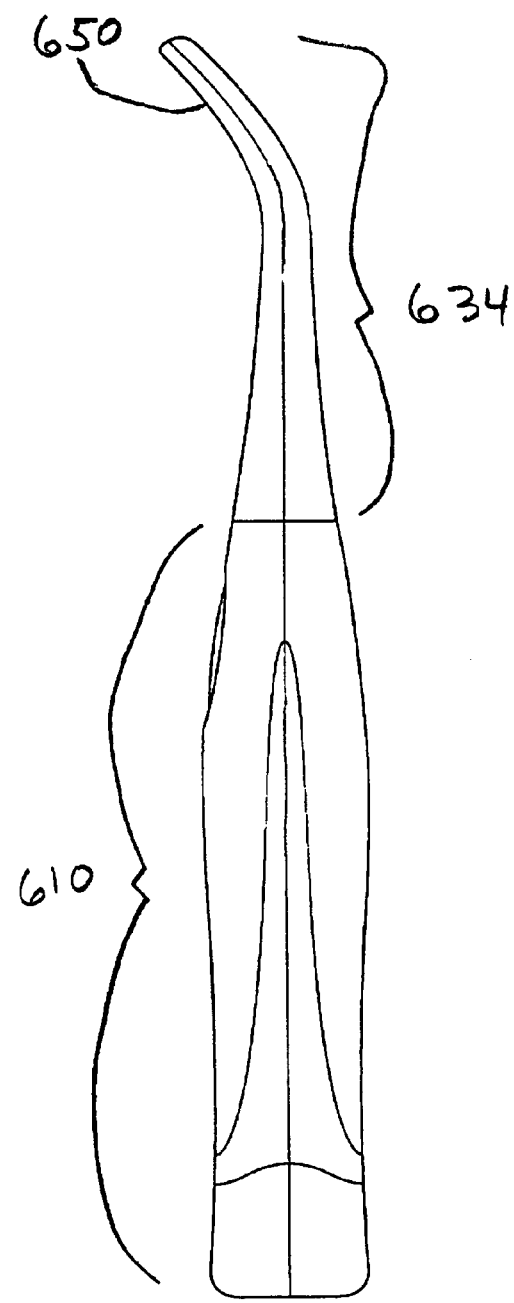
Fig. 7
Fig. 8

VIBRATORY CLEANING DEVICES AND METHODS

This application claims the benefit of U.S. provisional application No. 60/485,361 filed on Jul. 2, 2003, U.S. provisional application No. 60/523,046 filed on Nov. 17, 2003, and U.S. provisional application 60/540,866 filed on Jan. 30, 2004.

FIELD OF THE INVENTION

The field of the invention is dental hygiene.

BACKGROUND OF THE INVENTION

Motor powered toothbrushes have been known for many years. While such brushes can certainly provide more brushing movements over a given period of time, and therefore at least arguably "better brushing", the earliest electric toothbrushes were deficient in that they merely reciprocated in an up and down fashion.

U.S. Pat. No. 3,183,538 disclosed a significant improvement in toothbrush technology through the use of vibration instead of reciprocation. Among other things, vibration provided superior cleaning because the bristles of the toothbrush moved in all directions.

U.S. Pat. No. 3,466,689 took the concept of cleaning using vibration one step further by teaching a "sonic" dental cleaning device. In devices according to the '689 patent, the vibration was produced by an eccentric weight revolving about an axis at a frequency of 90–100 cycles per second. That frequency was apparently high enough to cause a sensation known as "acoustic streaming", i.e., localized high velocity streams of fluid created by high frequency sound in a liquid.

One problem with the '689 devices is that they failed to adequately clean the interproximal surfaces of the teeth. That problem was addressed in reissued U.S. Pat. No. Re.35,712, in which a vibrating toothbrush is combined with dental floss to clean interproximal surfaces of teeth. As it turned out, the idea was good but the execution was poor. The '712 patent taught the use of sonic frequencies between 2,000 and 20,000 cycles per minute, which were produced by an eccentrically mounted disc are in the handle. That arrangement imparted a significant amount of vibration to the hand of the user. An arrangement that imparts a significant amount of vibration to the hand of the user is inefficient, because the user's hand dampens the vibration causing less vibratory energy to be imparted to the dental floss. Such an arrangement is also uncomfortable because the user's hand is vibrating significantly.

Another problem is that devices according to the '712 patent had no supply of floss for restringing between the tines. In retrospect, that failure was entirely predictable from the way in which toothbrushes and dental floss evolved. The dental floss attachment was merely an "add-on" to a handle designed to vibrate a toothbrush. Since the toothbrush attachment was quite small, it was natural to provide a dental floss attachment that was also quite small, and therefore had no provision to store a supply of floss. In addition, since it was contemplated that a user would replace the toothbrush and flossing attachments during each use, it was natural to assume that the user would not object to utilizing an entirely new flossing attachment at each cleaning session.

U.S. Publication No. US 2002/0106607 does provide a vibrating flosser that has on-board supply of replacement floss. In that publication the inventor contemplated the supply as an externally mounted reel of floss, which is of course consistent with the prevailing notion of minimizing the size of the flossing attachment, and using the handle to enclose a relatively large motor and battery. But an external supply of floss has its own problems. Among other things an external supply of floss is aesthetically unappealing, and can readily accumulate toothpaste and other fluids. Thus, there is still a need to provide a vibrating flosser that has an internal supply of replacement floss.

SUMMARY OF THE INVENTION

The present invention is directed toward a flossing device having an internal supply of replacement floss, a pair of tines between which a measure of the floss is strung, and a vibration source that causes the floss to vibrate at a frequency of least 10 Hz. It is contemplated that the vibration source can comprise an eccentric weight and/or a buzzer (e.g. an electromagnetic buzzer).

In another aspect, the present invention is a cleaning device having at least three separable parts—a handle, a neck section, and an interchangeable cleaning head. The handle has a power source that is in electronic communication with the neck section, which houses a vibration source that is received by the interchangeable cleaning head.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWING

FIG. 1 is a side view of the front of a flossing device showing an activation button and a floss release button.

FIG. 2 is a side view of the back of the flossing device of FIG. 1, showing a motor inside the head.

FIG. 5 is a partially exploded side view of an alternative cleaning device, showing a handle, a neck section, and a razor head.

FIG. 6 is a partially exploded side view of another alternative cleaning device, showing a handle, a neck section, and a toothbrush head.

FIG. 7 is a side view of the cleaning device of FIG. 6 with a pick head.

FIG. 8 is a side view of the cleaning device of FIG. 6 with a tongue scraper head.

DETAILED DESCRIPTION

Figure 3:
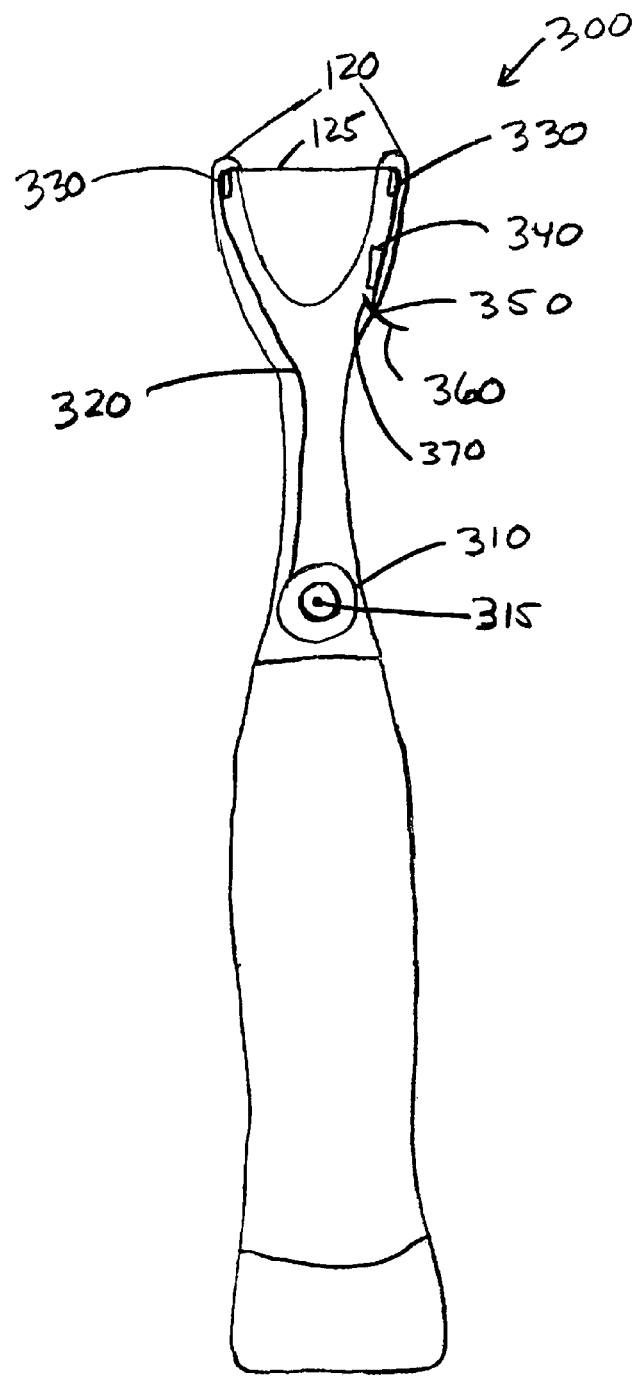
FIG. 3 is a side view of the back of the flossing device FIG. 1, with the cover of the head removed to reveal the internal supply of floss.

In FIG. 1, a flossing device 100 generally comprises a head 110 with a pair of tines 120 and a handle 130. The handle 130 has an activation button 140 and the head 110 has a floss release button 150.

As shown in FIG. 2, depressing activation button 140 causes power to be supplied to the device by closing an electrical circuit. A device can also be activated using any other suitable button, switch, dial, and so on. Preferably, rechargeable batteries 260 are located in the handle 130, and provide a source of power to a vibration source 245.

The vibration source 245 causes the length of floss 125 strung between the tines 120 to vibrate at a frequency of at least 10 Hz. In other more preferred embodiments, the length of floss vibrates at a frequency of at least 100 Hz, at least 1,000 Hz, at least 10,000 Hz, and at least 20,000 Hz. Vibration frequency can be fixed, or controlled with a multi-setting switch or dial 515 (shown in FIG. 5). At higher frequencies it can be advantageous to supply water or mouthwash to act as a coolant and/or a lavage.

In addition to the activation button 140, the front of a flossing device also shows a floss release button 150. A floss release button generally allows for tensioning and release of tension to the measure of floss 125 set between tines 120. Holding and release of the floss 125 is described in more detail below with reference to FIG. 4.

FIG. 2 depicts a flossing device with the head cover 112 removed to reveal an internally disposed electric motor 240 with connections 250 that couple to a power source 260 in handle 130.

Motor 240 is coupled to an eccentrically mounted disc 245, which rotates about a shaft (not shown) extending from the motor. Rotation of the disc 245 imparts vibrational energy to the floss 125 strung between the tines 120. It should be noted that the motor 240 and eccentrically mounted disc 245 are disposed high in the head 110— relatively close to the tines, so that a large percentage of the vibrational energy is transmitted to the tines 120. Advantageously, the motor 240 and disc 245 are housed within 4 cm of the length of floss strung between the tines 120. However, in less preferred embodiments the vibration source and/or the internal supply of floss can even be housed outside the head.

Alternative sources of vibrational energy are also contemplated. Thus, while an eccentrically mounted disc is a preferred source of vibrational energy, other vibratory sources can be employed such as an electromagnetic buzzer (see for e.g. www.american-audio.com examples of buzzers) or a piezoelectric motor.

In FIGS. 1–4 the handle 130 and head 110 are completely separable by a user. In preferred embodiments such separation can be accomplished readily, without use of any tools. Thus, if the head and handle were threaded together, detachment of the head from the handle would simply involve rotating the head relative to the handle until all of the threads were disengaged. Once the threads were completely disengaged, the head would then be separate from the handle and no connection between the two components would exist, especially no electrical connection. Of course, when the handle 130 and head 110 are coupled together, connections 250 are configured so that they provide power to the vibration source.

In FIG. 3, the flossing device 300 is shown, with the head cover 112 removed to reveal an internal supply of floss 310 (a spool) mounted on a spindle 315. The floss 320 follows a path (e.g. in a channel) up through the head 110 to the top of the tines 120, around floss holding elements 330, and finally out a small aperture 114 in the head covers 112 at point 350. Holding elements 330 and floss advancing mechanism 340 are mechanically coupled to floss release button 150. The functionality of the holding elements and advancing mechanism are discussed in more detail with reference to FIG. 4.

The internal supply of floss 310 is installed by removing the head cover 112 and sliding the supply of floss onto the spindle 315. The relative ease with which a supply of floss is removed and replaced is beneficial in a case where two people use the device, yet have different preferences for the type and or flavor of floss.

Excess or used floss 360 can be trimmed by a small cutting blade 370. It is preferred, that the cutting blade be substantially housed inside the head so as to reduce the chance of injuring a person using the device.

Figure 4:
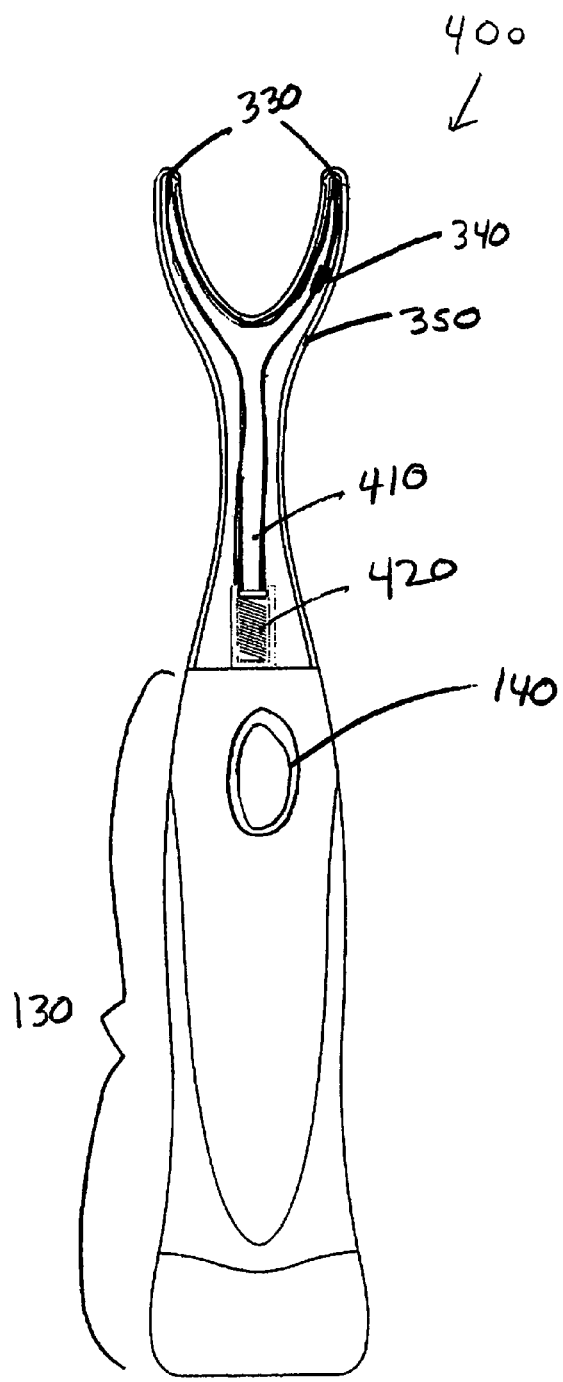
FIG. 4 is a side view of the front of the flossing device FIG. 1, with the cover of the head removed to reveal the floss release mechanism.

FIG. 4 depicts a flossing device 400, which shows the internal operation of the floss holding elements 330 and floss advancing mechanism 340 in relation to the floss release button 140.

Head 110 contains a generally "Y" shaped release component 410 that is coupled to a spring 420 or other biasing element. The spring 420 is compressed by manipulation of floss release button 150, and decompressed by release of the button 140. Thus, manipulating floss release button 150 causes spring 420 to compress, which in turn moves release component 410 in a direction toward the handle 130. This movement causes floss holding elements 330 to open, and tension on the floss to decrease. Movement of the release component 410 toward the handle 130 also causes floss advancing mechanism 340, which is coupled to the release component 410, to exert downward tension on the floss in a direction toward exit point 350. With the floss release button 140 actuated, the floss can be grasped by a user and freely extended and pulled out of the aperture 114 in the head cover 110.

FIG. 5 depicts a cleaning device 500 having three separable sections—a handle 510, a neck section 520, and an interchangeable cleaning head 530. The handle 510 houses a power source 512; the neck section 520 is in electrical communication with the handle 510 and houses a vibration source 525; and the interchangeable cleaning head receives the vibration source.

Interchangeable cleaning head 530 has a cavity 532 into which extends a portion of neck 520 (i.e. the portion having the motor and/or vibration source). Once received in the cavity 532, the vibration source 525 is within 4 cm of the top 540 of the cleaning device, although in more preferred embodiments, the vibration source is within 2 cm of the top of the cleaning device, and in yet more preferred embodiments, within 1 cm. Although the cleaning head 530 depicted in FIG. 5 comprises a razor blade 535 for shaving, many other heads are contemplated, including a head with coarse and/or firm bristles, a head with an abrading material, a head with a polishing material, a head with a pick for teeth 640, a head with a tongue scraper 650, and a head with a length of dental floss.

In a class of embodiments having a dental floss head, it is envisaged that the dental floss head will house both an internal supply of floss, and a vibration source, and therefore, no separable neck section will be necessary. In that class of embodiments, the floss is likely to be loaded into the head through the bottom of the separable head section— without the need to remove a head cover.

It is important to appreciate that although neck section 520 is separable from both the head 530 and the handle 510 the vibration source 525 is still proximate to the functional portion of the head—the razor blade 535. This three-section configuration is cost-effective and efficient. The configuration places the vibration source 525 near the functional portion 535 of the head 530, while eliminating the need for a different vibration source and/or motor for each interchangeable head.

FIG. 6 shows the cleaning device 600 with a toothbrush head 630. Head 630 is readily removable by applying an upward pressure to pull the head over seal 610. In FIG. 6 seal 610 is an annular rubber o-ring, however, attachment of the head 630 to the neck 620 and the neck 620 to the handle 610 can be accomplished using other means especially by threading.

Again, one of ordinary skill in the art will recognize that other types of motors and vibration sources can be used in a three-section embodiment, so long as the vibration source is housed in the separable neck section and received in the head.

FIG. 7 shows the cleaning device of FIG. 6 with a pick head 632 in place of the toothbrush head 630. Neck section 620 is not visible in FIG. 7, because neck section 620 is received within head section 632.

Pick 640 is constructed of rubber. In less preferred embodiments, a pick can be constructed of other suitable material. The pick 640 is shaped to have a substantially pointed tip that can be used on the interproximal areas between teeth. A pick can also take on other shapes and sizes so long as the pick remains suitable for interproximal use.

FIG. 8 is a side view of the cleaning device of FIG. 6 with a tongue scraper head 634 in place of the toothbrush head 630.

The tongue scraper head 634 has a tongue scraper component 650 that is used to scrape a user's tongue in order to reduce bacteria that causes bad breath. A tongue scraper component is preferred to be relatively flat so as to reduce gagging. Additionally, a preferred tongue scraper has a surface that is at least partially abrasive so that a user can remove bacteria by scraping the surface of his tongue.

Methods of flossing teeth include the steps of: providing a flossing device having an internal supply of floss; and vibrating a measure of the floss at a rate of at least 10 Hz. Alternative and/or additional methods can include the step of advancing the floss by actuating a floss release mechanism.

Methods of cleaning using a device described herein are also contemplated. Such methods of cleaning require the steps of: providing a vibration source in a separable neck section; and receiving the vibration source within the cleaning head.

Thus, specific embodiments and applications of the inventive subject matter have been disclosed. It should be apparent, however, to those skilled in the art that many more modifications besides those already described are possible without departing from the inventive concepts herein. The inventive subject matter, therefore, is not to be restricted to the embodiments disclosed herein. Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced.

What is claimed is:

1. A flossing device, comprising:
an internal supply of floss;
a pair of tines between which a length of the floss is strung;
movable floss holding elements disposed at distal tips of the tines to securely hold the floss;
a vibration source that causes the floss to vibrate at a frequency of at least 10 Hz, and
a user-operable actuator coupled to the tines that changes a tension of the length of the floss without unwinding or winding the floss.

2. The device of claim 1, wherein the frequency is least 100 Hz.

3. The device of claim 1, wherein the frequency is at least 1,000 Hz.

4. The device of claim 1, wherein the frequency is at least 20,000 Hz.

5. The device of claim 1, wherein the vibration source comprises an eccentric weight.

6. The device of claim 1, wherein the vibration source comprises an electromagnetic buzzer.

7. The device of claim 1, further comprising a cutting blade positioned on one of the tines.

8. The device of claim 1, further comprising a spindle upon which the supply of floss is mounted.

9. The device of claim 1, wherein the supply of floss is housed in a head.

10. The flossing device of claim 1, wherein the vibration source is housed in a head.

11. The device of claim 1 further comprising an actuating member disposed within a neck region of the device, wherein the actuating member moves toward a handle of the device to cause the floss holding elements to release the hold on the floss, thereby decreasing the tension.

12. The device of claim 1, further comprising a movable floss advancing mechanism that holds the floss and feeds the tip through an aperture in a direction from inside the device to outside the device.

13. The device of claim 1, wherein the user-operable actuator is coupled to the tines and instantly decreases the tension.

14. A flossing device, comprising:
a pair of tines between which a length of a floss is strung;
a quick-release mechanism having an actuating and disposed within a neck of the flossing device;
a floss advancing mechanism disposed on the actuating arm;
an aperture disposed on the device;
wherein the floss advancing mechanism directs and feeds the floss trough the aperture in a direction from inside the device to outside the device; and
wherein movement of the actuating and releases a tension of the length of the floss.

15. The device of claim 14 further comprising a vibration source coupled to the tines.

* * * * *